United States Patent [19]

Coates

[11] Patent Number: 4,766,122
[45] Date of Patent: Aug. 23, 1988

[54] CYANOAMIDINE COMPOUNDS AND DERIVATIVES THEREOF

[75] Inventor: William J. Coates, Welwyn Garden City, England

[73] Assignee: Smith Kline & French Laboratories Limited, Welwyn Garden City, United Kingdom

[21] Appl. No.: 844,426

[22] Filed: Mar. 26, 1986

[30] Foreign Application Priority Data

Mar. 27, 1985 [GB] United Kingdom ................. 8507941
Apr. 15, 1985 [GB] United Kingdom ................. 8509605

[51] Int. Cl.$^4$ .................... C07D 237/04; A61K 31/50
[52] U.S. Cl. ........................................ 514/247; 544/239
[58] Field of Search ................. 514/247; 544/238, 239

[56] References Cited

U.S. PATENT DOCUMENTS

| 3,475,431 | 10/1959 | Bachmann et al. | 544/238 |
| 3,746,712 | 7/1973 | Ross et al. | 260/250 |
| 4,397,854 | 8/1983 | Sircar | 424/250 |
| 4,503,061 | 3/1985 | Bristol et al. | 514/338 |
| 4,521,415 | 6/1985 | Katakami et al. | 514/252 |
| 4,523,011 | 6/1985 | Katakami et al. | 544/238 |
| 4,654,342 | 3/1987 | Slater | 514/247 |

FOREIGN PATENT DOCUMENTS

| 124314 | 4/1984 | European Pat. Off. . |
| 145019 | 12/1984 | European Pat. Off. . |
| 150937 | 11/1985 | European Pat. Off. . |

OTHER PUBLICATIONS

C A, vol. 106(11), 84625a, (1986).
Peterson, Journal of Medicinal Chemistry, vol. 17, No. 1, pp. 101–104, (1974).

Primary Examiner—Nicholas S. Rizzo
Attorney, Agent, or Firm—Edward T. Lentz; Janice E. Williams; Alan D. Lourie

[57] ABSTRACT

The invention relates to cyanoalkanimidamido derivatives that have utility as cardiac stimulants. A compound of the invention is 6-[4-($N^2$-cyanopropanimidamido)phenyl]-5-methyl-4,5-dihydro-3(2H)-pyridazinone.

18 Claims, No Drawings

CYANOAMIDINE COMPOUNDS AND DERIVATIVES THEREOF

The present invention relates to cyano derivatives and in particular to cyanoalkanimidamido compounds. This invention further relates to pharmaceutical compositions containing them and a method of stimulating cardiac activity by administering them. The compounds of this invention are phosphodiesterase type III inhibitors and are of use in combatting such conditions wherein such inhibition is thought to be beneficial. The compounds of this invention are positive inotropic agents and vasodilators with an extended duration of action and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The major utility of the compounds of this invention is in the treatment of congestive heart failure, for such treatment the compounds have a very desirable profile of activity.

Congestive heart failure is traditionally treated with cardiac glycosides, for example digoxin and digitoxin, and sympathomimetic agents. The glycosides have pronounced toxic effects with a low therapeutic index. The sympathomimetic agents generally do not have the desired profile of activity and are not orally effective. Amrinone is a marketed compound of interest that is reported to be an inotropic agent. This has an undesirable profile of side-effects when administered orally and development is being restricted to other modes of administration. Clearly there is a continuing need for orally active inotropic agents that have a good therapeutic profile.

Accordingly the present invention provides compounds of the formula (I):

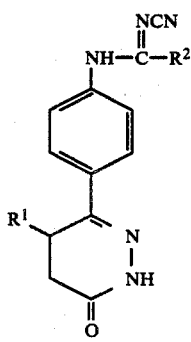

and pharmaceutically acceptable salts thereof, wherein
$R^1$ is hydrogen or methyl; and
$R^2$ is $C_{2-4}$ alkyl.

Suitably $R^1$ is hydrogen. Preferably $R^1$ is methyl.
Suitably $R^2$ is n-propyl or isopropyl. Preferably $R^2$ is ethyl.

A particular compound of the invention is 6-[4-($N^2$-cyanopropanimidamido)phenyl]-5-methyl-4,5-dihydro-3(2H)-pyridazinone.

The compounds of the invention are depicted as dihydropyridazin-3(2H)-ones, but of course the present invention covers all tautomeric forms thereof, for example the dihydropyridazinol form.

Furthermore the present invention covers all the optical isomeric forms of the compounds of the formula (I) in the racemic and separated forms. In particular when $R^1$ is methyl the (R) isomers of the compounds of the formula (I) (vide infra) are preferred.

Compounds of the formula (I) may form pharmaceutically acceptable salts with metal ions, such as alkali metals for example sodium and potassium, or alkaline earth metals for example calcium and magnesium.

In order to use a compound of the formula (I) or a pharmaceutically acceptable salt thereof for the treatment of humans and other mammals it is normally formulated in accordance with standard pharmaceutical practice as a pharmaceutical composition.

Compounds of formula (I) and their pharmaceutically acceptable salts may be administered in standard manner for the treatment of the indicated diseases, for example orally, parenterally, trans-dermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of a compound of formula (I)

or a pharmaceutically acceptable salt thereof calculated as the free base.

The daily dosage regimen for oral administration is suitably about 0.01 mg/Kg to 12 mg/Kg, of a compound of formula (I) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (I) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the invention are also bronchodilators and are useful in chronic obstructive lung disease for example asthma and bronchitis. Such conditions can be treated by administration orally, rectally, parenterally or by inhalation. For administration by inhalation dosages are controlled by a valve, are administered as required and for an adult are conveniently in the range 0.1–5.0 mg of a compound of the formula (I) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (I) or pharmaceutically acceptable salts thereof may be prepared by a process which comprises:

(a) reacting a compound of the formula (II) with a compound of the formula (III):

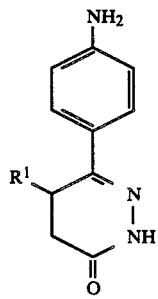
(II)

$$L^1-\underset{\underset{NCN}{\parallel}}{C}-R^2 \quad (III)$$

wherein $R^1$ and $R^2$ are as hereinbefore defined, and $L^1$ is a leaving group; or (b) reacting a compound of the formula (IV) with cyanamide or a heavy metal salt thereof:

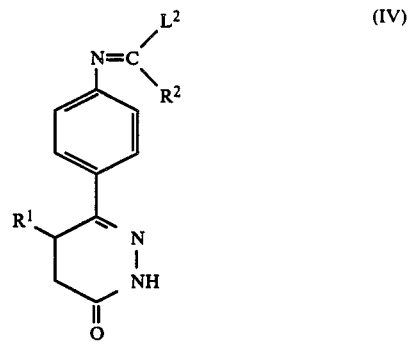
(IV)

wherein $R^1$ and $R^2$ are as hereinbefore defined, and $L^2$ is a displaceable group; or (c) reacting a compound of the formula (V) with hydrazine or chemical equivalent thereof:

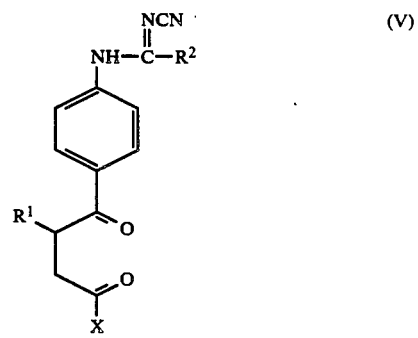
(V)

wherein $R^1$ and $R^2$ are as hereinbefore defined, and X is a leaving group: and thereafter optionally forming a pharmaceutically acceptable salt.

In the reaction between the compounds of the formulae (II) and (III), suitably $L^1$ is benzylthio or $C_{1-6}$alkylthio for example methylthio. Such a reaction is conveniently performed in a solvent such as pyridine at an elevated temperature for example under conditions of reflux. In a suitable alternative $L^1$ is $C_{1-6}$alkoxy, phenoxy or benzyloxy, preferably phenoxy. Such a reaction is conveniently performed in an aprotic organic solvent such as dimethylformamide, or a $C_{1-4}$alkanol for example ethanol, at an elevated temperature, for example between 50° C. and 150° C., preferably between 70°–130° C.

The compounds of the formula (II) are known from U.S. Pat. Nos. 3,746,712 and 3,475,431.

The (R) and (S) isomers (respectively the (−) and (+) isomers) of the compound of the formula (II) wherein $R^1$ is methyl can be separated by passage of racemic compound over a chiral phase chromatography column. The appropriate fractions are collected, rechromatographed as necessary, solvent is evaporated and the desired isomer isolated in conventional manner.

In the reaction of a compound of the formula (IV) and cyanamide or a heavy metal salt thereof, suitably $L^2$ is mercapto (—SH), i.e. tautomeric with thioacetamido, and can be reacted with a heavy metal salt of cyanamide, for example, a lead, mercury or cadmium salt. Conveniently such reactions can be carried out in acetonitrile or dimethylformamide. In an alternative in the compounds of the formula (IV) $L^2$ can be $C_{1-4}$alkylthio, $C_{1-4}$alkoxy, phenoxy or benzyloxy. Such compounds can be reacted with cyanamide in the presence of a strong base for example those having anions of weak nucleophilic character such as sodium hydride or potassium t-butoxide. Suitably the reaction is carried out in a solvent under anhydrous conditions and preferably at an elevated temperature for example 60° C.-120° C., conveniently at the reflux temperature of a $C_{1-4}$alkanol. When potassium t-butoxide is the strong base it is convenient to use t-butanol as solvent. Preferably $L^2$ is $C_{1-4}$alkylthio or $C_{1-4}$alkoxy for example ethoxy.

The compounds of the formula (IV) can be prepared in conventional manner from a compound of the formula (II), for example reacting with a compound: $L^3L^4CL^2R^2$ wherein $R^2$ is as hereinbefore defined, $L^2$ is $C_{1-4}$alkoxy and $L^3$ and $L^4$ are groups sequentially displaceable by aniline. For example when $L^2$ is ethoxy a compound of the formula (II) can be reacted with triethyl orthopropionate.

The compounds of the formula (IV) wherein $L^2$ is mercapto (—SH) can be prepared from a compound of the formula (II) by reaction with a compound: $R^2L^5C=S$ wherein $R^2$ is as hereinbefore defined and $L^5$ is a group displaceable by aniline such as halo.

The compounds of the formula (IV) wherein $L^2$ is $C_{1-4}$alkylthio can be prepared from a compound of the formula (IV) wherein $L^2$ is mercapto by reaction with a $C_{1-4}$alkylating reagent.

The resolved form of a compound of the formula (I) can be prepared from the corresponding resolved form of a compound of the formula (II) either directly or via the resolved form of a compound of the formula (IV) in an analogous manner to that described for preparing a compound of the formula (I) from a compound of the formula (II).

The reaction between a compound of the formula (V) and hydrazine or a chemical equivalent thereof is suitably performed at ambient or elevated temperature, for example 15° C.-120° C., preferably about 30° C.-80° C. or at reflux temperature of a suitable solvent. The reaction is conveniently performed in a solvent such as a $C_{1-4}$alkanol for example methanol, ethanol or n-propanol, or aqueous or glacial acetic acid. Suitably in the compounds of the formula (V) X is hydroxy, $C_{1-6}$alkoxy, amino or $C_{1-6}$alkylamino.

By a chemical equivalent of hydrazine we mean hydrazine hydrate, hydrazine ethanolate or a similar solvate. Preferably hydrazine is used in the form of hydrazine hydrate.

The compounds of the formula (V) can be prepared by reacting a compound of the formula (VI):

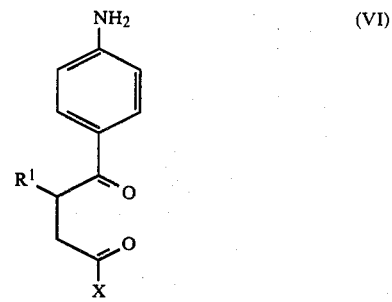

wherein $R^1$ and X are as hereinbefore defined with a compound of the formula (III) as hereinbefore defined; in an analogous manner to that described for reacting compounds of the formulae (II) and (III). The compounds of the formula (VI) are known or preparable in conventional manner, see for example the above identified U.S. Patents and Curran et al., J. Med. Chem., 17, p 273 (1974).

Pharmaceutically acceptable base addition salts of the compounds of the formula (I) may be prepared by standard methods, for example by reacting a solution of the compound of the formula (I) with a solution of the base.

The following biological test methods, data, Description and Examples serve to illustrate this invention.

Cardiac Stimulant Activity - In vitro

The compounds of formula (I) and their pharmaceutically acceptable salts are tested for cardiac stimulant activity following a procedure based on that of S.C. Verma and J. H. McNeill (J. Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 50 ml bath containing Krebs Henseleit solution at 37° C., and the bath is bubbled with 95% oxygen and 5% carbon dioxide. The ventricular strips are electrically stimulated at a frequency of 1.0 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% ($EC_{50}$) increase in the force of contraction of the ventricular strips at concentrations in the bathing fluid of less than $10^{-4}$ molar, thus showing that they have activity as positive inotropic agents.

In the above test method the compound of Example 1 gave an $EC_{50}$ value of $0.065 \times 10^{-6}$M. In comparison amrinone gave a value of $15 \times 10^{-6}$M.

Cardiac Stimulant Activity - In vivo (Anaesthetised Cats)

In anaesthetised cats pretreated with a ganglion blocker (pempidine) and propranolol, the compounds of the Examples caused sustained increases in left ventricular dp/dt max (this is an index of left ventricular contractility) when administered intravenously. The dose to increase left ventricular dp/dt max by 50% is given as the $ED_{50}$. The compound of Example 1 gave an ED$_{50}$ (micromol/kg) value of 0.02 and displayed a long duration of activity. In comparison amrinone gave a value of 5.6 and displayed a short duration of activity.

Inhibition of Phosphodiesterases

Three peaks of cyclic nucleotide phosphodiesterase activity [PDE (Peak I), PDE (Peak II) and PDE (Peak III)] from cat heart were separated by chromatography on DEAE-Sepharose CL-6B (Diethylaminoethyl Cellulose with a bead size of 45-165 microns). Sepharose is a registered trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a 15×1.5 cm column of DEAE-Sepharose equilibrated with the homogenisation buffer. The PDE activities were eluted with a gradient of 0.05-1 M Na acetate in 20 mM PIPES. There were three major peaks which had the following characteristics:

| PDE (Peak I) - eluted at 0.15 M Na acetate | | | |
|---|---|---|---|
| Substrate | 50 μg/ml calmodulin (+ = added) | Km (μM) | Relative V$_{max}$ |
| cyclic AMP | − | 0.5 | 1 |
| cyclic GMP | − | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
|---|---|---|
| Substrate | Km (μM) | Relative V$_{max}$ |
| cyclic AMP | 6 | 1 |
| cyclic GMP | 28 | 0.2 |

| PDE (Peak III) - eluted at 0.5 M Na acetate | | |
|---|---|---|
| Substrate | Km (μM) | Relative V$_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by Ca$^{2+}$/calmodulin complex.

PDE (Peak II) demonstrates relatively low affinities for both cyclic AMP and cyclic GMP and is not affected by Ca$^{2+}$/calmodulin complex.

PDE (Peak III) has high affinity for cyclic AMP. It can also hydrolyse cyclic GMP though the preferred substrate is cyclic AMP. This activity is also insensitive to Ca$^{2+}$/calmodulin activation.

Enzyme assay

The enzyme was assayed by incubation at 37° for 4-30 min in 50 mM Tris, 5 mM MgCl$_2$, pH 7.5 with [3-H]cyclic nucleotide (4×10$^5$ disintegrations min$^{-1}$) and [14-C]nucleotide 5' monophosphate (3×10$^3$ disintegrations min$^{-1}$). The assay was stopped by boiling, and the [3-H]5' monophosphate product separated from substrate on boronate columns (Davis, C. W. and Daly, J. W. (1979) J. Cyclic Nucleotide Res., 5, 65-74). The reaction mixture was diluted with 0.5 ml 100 mM HEPES (N-2-Hydroxyethyl-piperazine-N'-2-ethanesulfonic acid), 100 mM NaCl, pH 8.5, and applied to the column. The column was extensively washed with the same buffer, and the 5' nucleotide eluted with 6 ml 0.25 M acetic acid. The recovery of product as judged by [14-C]recovery was approximately 80%. All assays were linear with time of incubation and concentration of enzyme over the range used in these experiments.

Calculation of IC$_{50}$ values

IC$_{50}$ values (the concentration of inhibitor required for 50% inhibition of activity) were obtained for PDE (Peak III) by incubation of the enzyme at 1 μM cyclic AMP, and a range of inhibitor concentrations from 0.1×IC$_{50}$ to 100×IC$_{50}$.

| Compound of Example | IC$_{50}$ × 10$^{-6}$ M |
|---|---|
| 1 | 0.08 |
| Amrinone | 51.8 |
| Milrinone | 2.2 |

Description 1

(+) and (−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (2.0 g) dissolved in a mixture of acetonitrile (80 ml) and dichloromethane (30 ml) was added to a column of ionically bound (R)-N-(3,5-dinitrobenzoylphenyl)glycine on 40 μm γ-aminopropyl silanized silica (2.1 kg), packed at 1104 kPa (160 p.s.i.) (by slurrying with dichloromethane (1.5 L)) in a Jobin-Yvon medium pressure liquid chromatography system. The column was eluted with dichloromethane/methanol (199:1) over 9 hours at a rate of 80 ml min$^{-1}$. Detection was by u.v. at 280 nm. A broad peak was obtained from which fractions were collected. The earlier fractions were enriched (−) enantiomer. These fractions were combined and re-chromatographed through the same column with the same eluant.

The selected column fractions were evaporated, triturated with diethyl ether, filtered and the resultant solid washed with diethyl ether and dried at 80° C. for 18 hours to give (−)-6-(4-aminophenyl)-5-methyl-4,5-dihydro-3(2H)-pyridazinone, in approximately 100% enantiomeric excess, m.p. 203°-4° C.; [α]$_D^{25}$=−399° [concentration 0.74% in ethanol:water:conc. HCl (17:2:1)].

A sample of the (−) isomer was reacted with 3-bromopropionyl chloride to afford enantiomerically pure (−)-6-[4-(3-bromopropionamido)phenyl]-5-methyl-4,5-dihydro-3(2H)-pyridazinone, the absolute configuration of which was shown by a X-ray diffraction study to be (R).

The later fractions from the first column were enriched (+) enantiomer (approximately 75% enrichment) which was subjected to medium pressure liquid chromatography (Jobin-Yvon system) over a column of ionically bound (S)-N-(3,5-dinitrobenzoyl)phenylglycine on 25-40 μm γ-aminopropyl silanized silica (55 g) eluting with dichloromethane/methanol (199:1). The appropriate fractions were combined with fractions from another run and re-chromatographed through the same column.

The selected column fractions were evaporated, triturated with diethyl ether, filtered and the resultant solid washed with diethyl ether and dried at 80° C. for 18 hours to give (+)-6-(4-aminophenyl)-5-methyl-4,5-dihydro3(2H)-pyridazinone, in approximately 100% enantiomeric excess, m.p. 206°-8° C.; [α]$_D^{25}$=+376° [concentration 0.74% in ethanol:water:conc. HCl (17:2:1)].

EXAMPLE 1

6-[4-($N^2$-Cyanopropanimidamido)phenyl]-5-methyl-4,5-dihydro-3(2H)-pyridazinone 6-(4-Aminophenyl)-5-methyl-4,5-dihydro-3(2H)-pyridazinone (2 g) and triethyl orthopropionate (2.5 g) were stirred with heating (150° C.) in an oil bath for 15 minutes. Ethanol was removed by distillation. The resultant syrup was cooled, cyanamide (0.8 g) added and the mixture heated for a further 15 minutes at 150° C. The mixture was cooled, stirred with ethanol, filtered and the solid (1.22 g) was collected. This solid was triturated with hot ethanol to give the title compound (0.39 g), m.p. 235–237° C. (recrystallised from ethanol).

EXAMPLE 2

(R)-6-[4-($N^b$ 2-Cyanopropanimidamido)phenyl]-5-methyl-4,5-dihydro-3(2H)-pyridazinone (R)-6-(4-Aminophenyl)-5-methyl-4,5-dihydro-3(2H)-pyridazinone and triethyl orthopropionate are stirred with heating (150° C.) in an oil bath for 15 minutes. Ethanol is removed by distillation. The resultant syrup is cooled, cyanamide added and the mixture heated for a further 15 minutes at 150° C. to afford the title compound.

EXAMPLE 3

Ethyl 3-[4-($N^2$-cyanopropanimidamido)benzoyl]butyrate

A mixture of ethyl 3-(4-aminobenzoyl)butyrate and ethyl N-cyanopropionimidate in ethanol is heated to afford the title compound.

EXAMPLE 4

Pharmaceutical compositions for oral administration are prepared by combining the following:

|  | % w/w | | |
| --- | --- | --- | --- |
| 6-[4-($N^2$—cyanopropanimidamido)phenyl]-5-methyl-4,5-dihydro-3(2H)—pyridazinone | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

What is claimed is:

1. A compound of the formula (I):

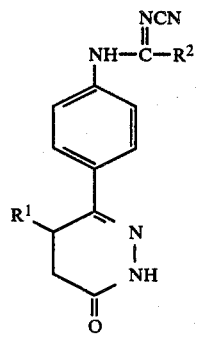

or a pharmaceutically acceptable salt thereof, wherein
$R^1$ is hydrogen or methyl; and
$R^2$ is $C_{2-4}$alkyl.

2. A compound according to claim 1 wherein $R^1$ is methyl.

3. A compound according to claim 1 wherein $R^2$ is ethyl.

4. A compound according to claim 1 which is: 6-[4-($N^2$-cyanopropanimidamido)phenyl]-5-methyl-4,5-dihydro-3(2H)-pyridazinone or a pharmaceutically acceptable salt thereof.

5. A compound according to claim 2 in which the (R) isomer is enantiomerically enriched.

6. The (R) isomer of a compound according to claim 2.

7. A compound according to claim 1 which is:
(R)-6-[4-($N^2$-cyanopropanimidamido)phenyl]-5-methyl-4,5-dihydro-3(2H)-pyridazinone or a pharmaceutically acceptable salt thereof.

8. A compound according to claim 1 which is:
(R)-6-[4-($N^2$-cyanopropanimidamido)phenyl]-5-methyl-4,5-dihydro-3(2H)-pyridazinone or a pharmaceutically acceptable salt thereof substantially free of the corresponding (S) isomer.

9. A pharmaceutical composition for stimulating cardiac activity which comprises an effective amount of a compound according to claim 1 and a pharmaceutically acceptable carrier.

10. A pharmaceutical composition for stimulating cardiac activity which comprises an effective amount of a compound according to claim 4 and a pharmaceutically acceptable carrier.

11. A pharmaceutical composition for stimulating cardiac activity which comprises an effective amount of a compound according to claim 7 and a pharmaceutically acceptable carrier.

12. A method for stimulating cardiac activity in a mammal comprising internally administering an effective amount of a compound according to claim 1.

13. A method for stimulating cardiac activity in a mammal comprising internally administering an effective amount of a compound according to claim 4.

14. A method for stimulating cardiac activity in a mammal comprising internally administering an effective amount of a compound according to claim 7.

15. A method for effecting bronchodilatation in a mammal comprising internally administering an effective amount of a compound according to claim 1.

16. A method for effecting bronchodilatation in a mammal comprising internally administering an effective amount of a compound according to claim 4.

17. A method for effecting bronchodilatation in a mammal comprising internally administering an effective amount of a compound according to claim 7.

18. A compound of the formula (IV):

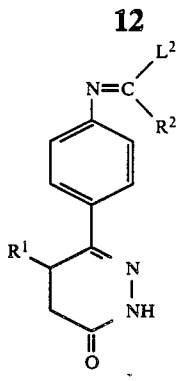
wherein
R$^1$ is hydrogen or methyl;
R$^2$ is C$_{2-4}$alkyl; and
L$^2$ is selected from the group consisting of mercapto (—SH), C$_{1-4}$alkylthio, C$_{1-4}$alkoxy, phenoxy or benzyloxy.
* * * * *